United States Patent
Florman

(10) Patent No.: US 9,561,161 B2
(45) Date of Patent: Feb. 7, 2017

(54) METHOD OF CLEANING AN ORAL APPLIANCE

(71) Applicant: Michael Florman, Pacific Palisades, CA (US)

(72) Inventor: Michael Florman, Pacific Palisades, CA (US)

(*) Notice: Subject to any disclaimer, the term of this patent is extended or adjusted under 35 U.S.C. 154(b) by 21 days.

(21) Appl. No.: 14/271,174

(22) Filed: May 6, 2014

(65) Prior Publication Data

US 2014/0335026 A1    Nov. 13, 2014

Related U.S. Application Data

(60) Provisional application No. 61/820,393, filed on May 7, 2013.

(51) Int. Cl.
| | | |
|---|---|---|
| *A61K 8/22* | (2006.01) | |
| *A61Q 11/00* | (2006.01) | |
| *A61K 8/04* | (2006.01) | |
| *A61Q 11/02* | (2006.01) | |

(52) U.S. Cl.
CPC ............... *A61K 8/22* (2013.01); *A61K 8/046* (2013.01); *A61Q 11/02* (2013.01)

(58) Field of Classification Search
USPC .............................. 424/50, 52, 53
See application file for complete search history.

(56) References Cited

U.S. PATENT DOCUMENTS

| | | | |
|---|---|---|---|
| 8,518,382 B2* | 8/2013 | Speronello | A61K 8/22 424/49 |
| 8,753,612 B2* | 6/2014 | De Vreese | A61K 8/0208 424/401 |

FOREIGN PATENT DOCUMENTS

| | | | | |
|---|---|---|---|---|
| WO | WO 97/10802 | * | 3/1997 | A61K 7/16 |

* cited by examiner

*Primary Examiner* — Walter Webb
(74) *Attorney, Agent, or Firm* — Tope-McKay & Associates

(57) ABSTRACT

A method of cleaning an oral appliance allows a dental patient or other oral appliance wearer to clean the appliance while the appliance is in place in the wearer's mouth. The appliance wearer dispenses a quantity of foamed, cleanser formulation into to his or her mouth, swishes the cleanser around in the mouth for a desired amount of time, and then expectorates any remaining cleanser. A cleaning kit for an oral appliance is also provided and includes a mixture of water, hydrogen peroxide, and at least one surfactant in a foam-dispensing bottle.

10 Claims, 4 Drawing Sheets

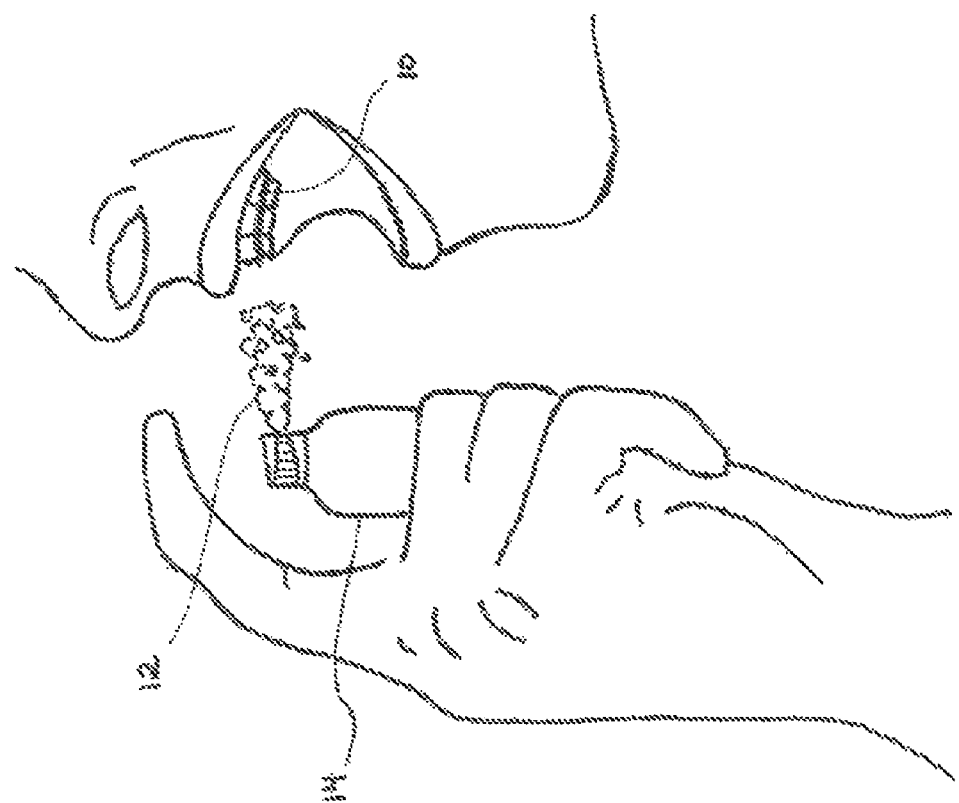

METHOD OF CLEANING AN ORAL APPLIANCE

CROSS-REFERENCE TO RELATED APPLICATION

This application claims the benefit of U.S. provisional application No. 61/820,393, filed May 7, 2013, the entire contents of which are incorporated herein by this reference.

BACKGROUND OF THE INVENTION

Dental appliances, such as orthodontic retainers, dental aligners (such as Invisalign®, ClearCorrect™, and other brands), dentures, sleep apnea appliances, sports mouth guards, etc., are often worn anywhere from 30 minutes to 23 hours a day or longer and accumulate food particles, saliva, dead gingiva (skin), and other detritus. Over time (ranging from minutes to hours), the dental appliance begins to smell bad and discolor. Currently, oral appliance cleaners are designed for use outside the mouth and require the appliance—dentures, retainers, mouth guards, etc.—to be soaked in the cleaning solution and sometimes cleaned in a sonic or ultrasonic cleaning device. Within 20 minute of being returned to the mouth, however, the appliance becomes dirty or contaminated again with food debris and microorganisms. A need exists for an oral appliance cleaner that can be used on the go, throughout the day if necessary, without requiring the appliance wearer to keep the appliance out of his or her mouth during the cleaning process.

SUMMARY OF THE INVENTION

According to a first aspect of the invention, a method of cleaning an oral appliance is provided that allows a dental patient or other oral appliance wearer to clean the appliance while the appliance is in the wearer's mouth. The appliance wearer simply dispenses a quantity of cleanser formulation into or onto the appliance and reinserts the appliance back into his or her mouth. If necessary, excess appliance cleanser is then expectorated. In an alternate embodiment, the oral appliance wearer applies the cleanser formulation to the appliance while the appliance is being worn; swishes cleanser formulation around in the mouth for a short time; and then expectorates any excess cleanser formulation. In another embodiment, the appliance wearer removes the appliance from his or her mouth; applies the cleanser formulation to the appliance; and places the appliance into a storage case. After allowing the appliance to dwell for 5 to 30 minutes, the appliance wearer retrieves the appliance from the storage case and reinserts it into his or her mouth, there being no need to rinse off any excess cleanser formulation. A primary benefit of the invention is its ease of use, as it offers the oral appliance wearer a quick way to clean the appliance while on the go, without having to clean the appliance in a separate vessel or under a stream of water.

The invention also provides a cleaning kit for an oral appliance that includes a foam-dispensing bottle filled with the cleanser formulation. In general, the cleanser formulation contains 70 to 98% water, 0.01 to 5% surfactant(s), and 0.01 to 30% hydrogen peroxide, and optionally one or more additional ingredients, with the amount of each ingredient being selected so that total ingredients sum to 100% by weight. Advantageously, the invention can be used without removing the oral appliance from the mouth, thereby ensuring that the beneficial use of the appliance is uninterrupted.

BRIEF DESCRIPTION OF THE DRAWINGS

FIG. 4 is a schematic illustration of an oral appliance with a foamed cleanser formulation thereon, seated in a storage case, according to one embodiment of the invention.

DETAILED DESCRIPTION

Figure 1:
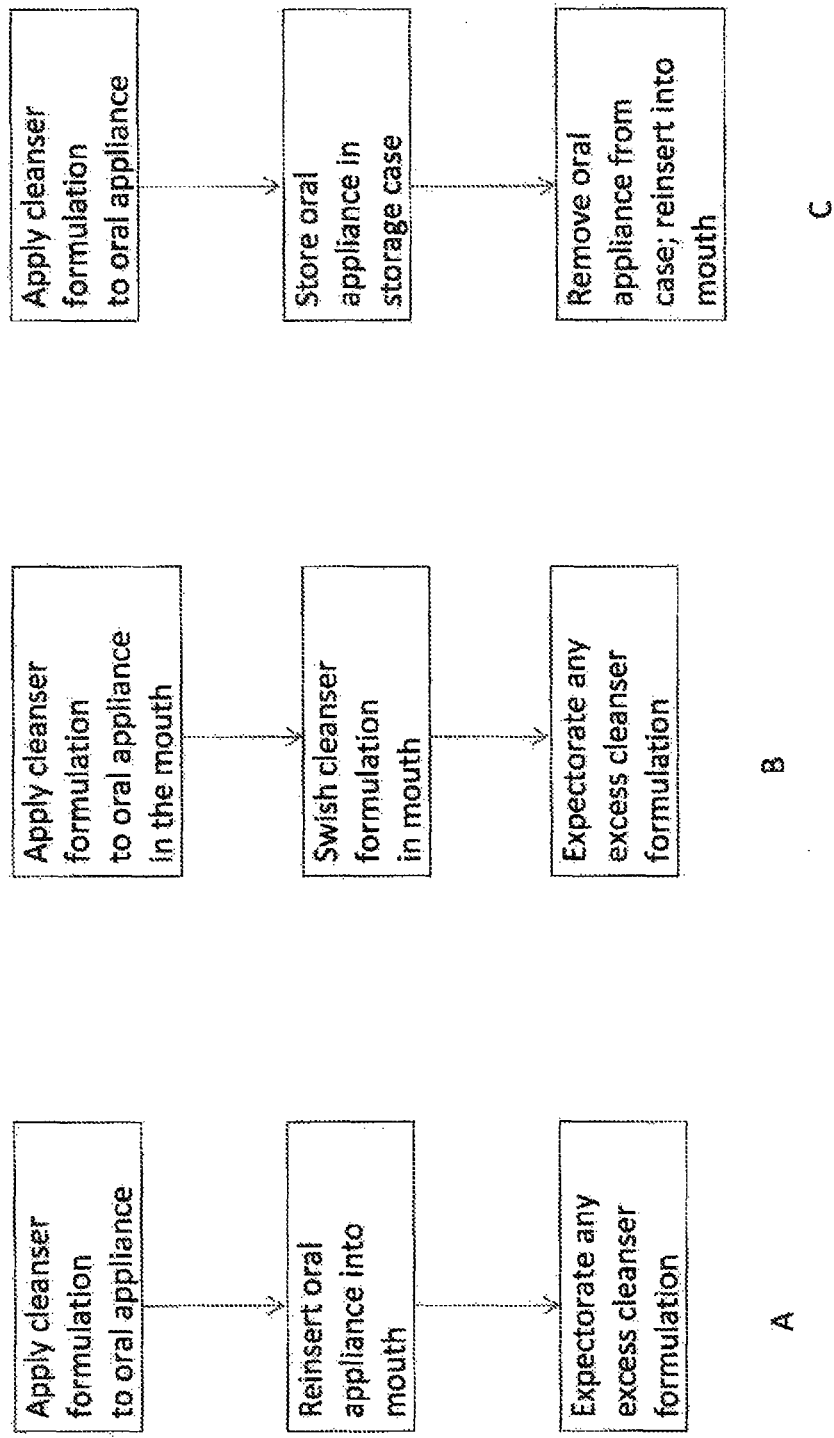
FIG. 1 is a flowchart illustrating three embodiments of a method of cleaning an oral appliance according to one aspect of the invention.

According to a first aspect of the invention, a method of cleaning an oral appliance is provided that allows a dental patient or other oral appliance wearer to clean the appliance while the appliance is in place in the user's mouth. FIG. 1 illustrates three embodiments of the cleaning method. In embodiment A, after removing the appliance from his or her mouth, the appliance wearer dispenses a quantity of cleanser formulation into or onto the appliance (step one); reinserts the appliance back into his or her mouth (step two); and, if necessary, expectorates any excess cleanser formulation (step three). As described below in greater detail, the cleanser formulation can be dispensed from a foam-dispensing bottle and applied to the appliance as a foam. In embodiment B, the oral appliance wearer applies the cleanser formulation directly to the appliance while the appliance is being worn (step one); swishes cleanser formulation around in the mouth for a short time; and, if necessary, expectorates any excess cleanser formulation (step three). In embodiment C, after removing the appliance from his or her mouth, the appliance wearer applies the cleanser formulation to the appliance (step one); places the appliance into a storage case (step two); and, after allowing the appliance to dwell for 5 to 30 minutes, retrieves the appliance from the storage case and reinserts it into his or her mouth (step three), there being no need to rinse off any excess cleanser formulation.

Figure 2:
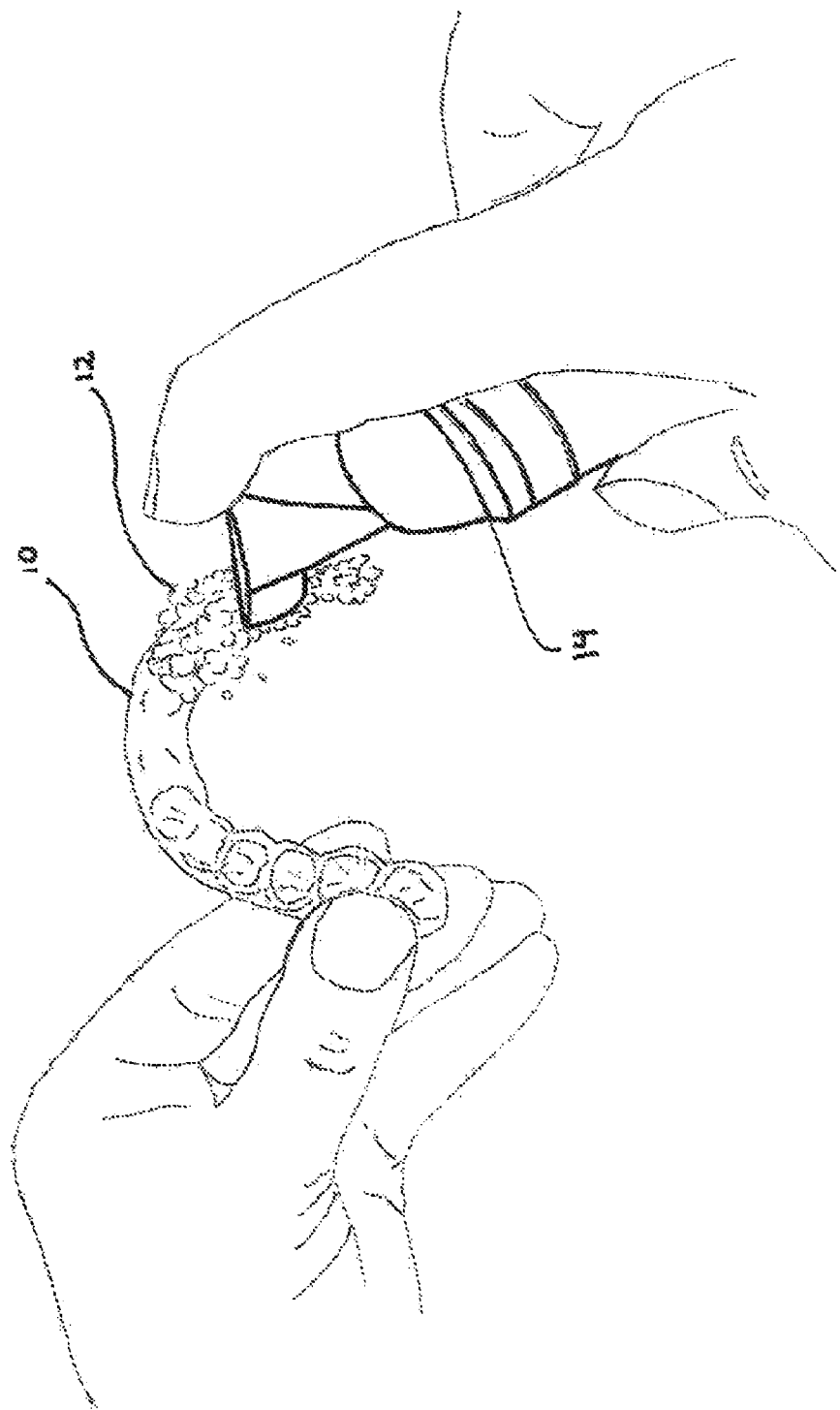
FIG. 2 is a schematic illustration of the application of a cleanser formulation according to one embodiment of the invention.
Figure 3:
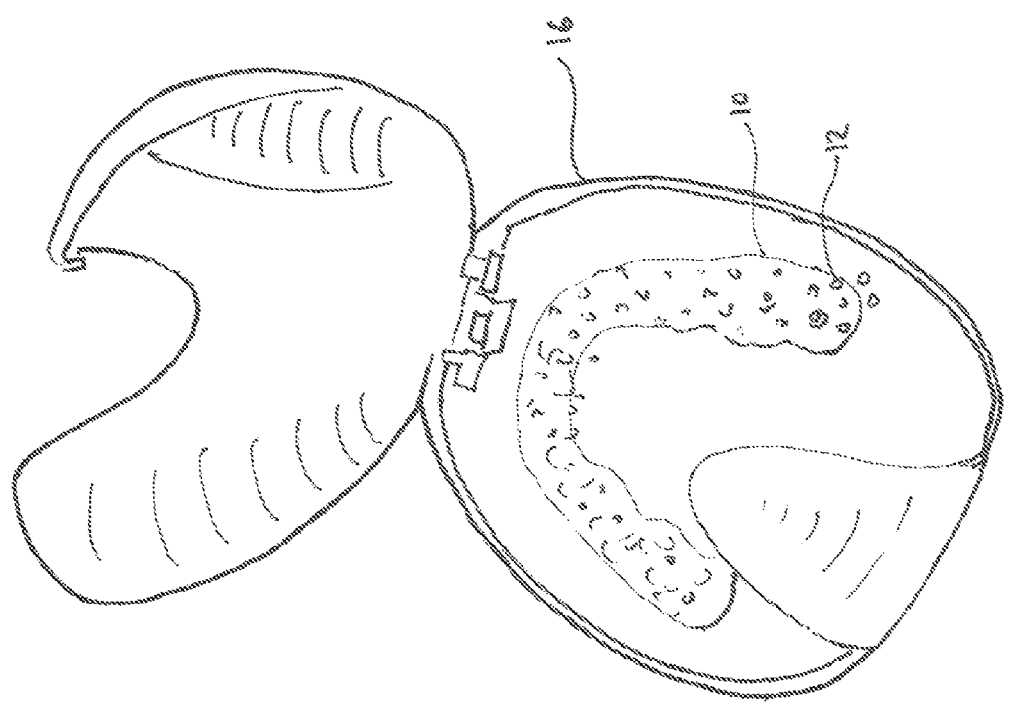
FIG. 3 is a schematic illustration of the application of a cleanser formulation according to another embodiment of the invention.

FIG. 2 illustrates the application of a cleanser formulation to an oral appliance according to one embodiment of the invention. After removing the oral appliance—in this case, an orthodontic aligner 10—from his or her mouth, the user dispenses a quantity of a cleanser formulation as a foam 12 from a foam-dispensing bottle 14. The foamed cleanser formulation is directed onto the aligner. Thereafter, the person reinserts the aligner back into his or her mouth (embodiment A). Alternatively, the user stores the aligner for a period of time in an aligner storage case 16, as shown in FIG. 3. After a short period of time, the user retrieves the clean aligner from the storage case and reinserts it into his or her mouth (embodiment C).

In embodiment B, shown in FIG. 4, the appliance wearer dispenses a quantity of foamed cleanser 12 from a foam-dispensing bottle 14, directly onto the oral appliance 10—in this case an orthodontic retainer. The user swishes the cleanser formulation around in his or her mouth and then expectorates any remaining cleanser formulation.

In one embodiment, the cleanser formulation contains, on a percent-by-weight basis, 70 to 98% water, 0.01 to 5% surfactant(s), and 0.01 to 30% hydrogen peroxide, with the amount of each ingredient selected so that total ingredients sum to 100% by weight. In a more preferred embodiment, the cleanser formulation also contains one or more additional ingredient: 0.01 to 4% sweetener(s), 0.01 to 4% ethylenediaminetetraacetate (EDTA), 0.01 to 6% sodium citrate or citric acid, and/or 0.01 to 3% flavorant(s), the amount of each ingredient being selected so that total ingredients sum to 100% by weight.

Hydrogen peroxide is a germicidal agent and a bleaching agent, and plays a primary role in cleaning the oral appliance. The surfactant(s) facilitate the formation of a foam, as described below, and have intrinsic cleaning properties. One or a combination of surfactants is employed, including anionic, non-ionic, zwitterionic, poloxamer, and/or polysorbate surfactants. Nonlimiting examples include sodium lauryl sulfate (anionic), sodium dodecyl sulfate (anionic), cocamidopropyl betaine (zwitterionic), poloxamer 188, poloxamer 338, poloxamer 407, polysorbate 20, and alkyl polyglucosides (non-ionic). In one embodiment, the foam cleaner formulation is sprayed onto the appliance in such a way that it will reside between the appliance and the user's teeth. This can be accomplished by spraying on the appliance outside the mouth and then placing the appliance in place or by spraying when the appliance is in place in the mouth and aiming the spray close to the spaces and areas of contact between the teeth and the appliance. In this mode the combination of the hydrogen peroxide and the surfactant act together to clean and maintain cleaning effect as well as whitening on both the appliance and the teeth.

Without being bound by theory, it is believed that EDTA facilitates the removal of inorganic debris (e.g., calcified deposits) through its chelating properties, and also functions as a preservative. Sodium citrate and citric acid are pH regulators and antioxidants. Preferred sweetener(s), if present, are those that do not promote tooth decay. Nonlimiting examples include xylitol, aspartame, sucralose, sorbitol, and saccharine. Nonlimiting examples of flavorants include peppermint, spearmint, wintergreen (methyl salicylate), cinnamon, vanilla, orange, and bubblegum.

Optionally, the cleanser formulation includes one or more additional ingredient. Unless otherwise indicated, each ingredient is present in an amount of from 0.01 to 6.0% by weight, with the amount of each ingredient being selected so that total ingredients in the cleanser formulation sum to 100% by weight. Nonlimiting examples of such additional ingredients include other peroxides, e.g., carbamide peroxide, calcium peroxide, and magnesium peroxide; ethanol (0.001 to 50%); potassium hydroxide (0.001 to 10%); food coloring; sodium bicarbonate; fluorides, including acidulated, stannous, and sodium fluoride (0.0001 to 5%); remineralizing agents, e.g., calcium phosphate, amorphous calcium phosphate (ACP), and other calcium chemicals; cetyl pyridinium chloride and related quaternary ammonium chlorides (0.001 to 3%); triclosan (0.001 to 5%); desensitizing agents, e.g., potassium nitrate, potassium citrate, potassium chloride, stannous fluoride, and strontium chloride (0.001 to 11%); anti-halitosis agents, e.g., chlorine dioxide, essential oils, and zinc chloride; tartar control agents, e.g., pyrophosphate, hexametaphosphate, zinc, zinc chloride; sorbitol; propylene glycol (0.001 to 33%); disodium phosphate (0.001 to 29%); eucalyptol (0.001 to 3%); menthol (0.001 to 3%), and thymol (0.001 to 3%). In one embodiment, the cleanser formulation contains only ingredients that are classified as Generally Recognized As Safe (GRAS) by the U.S. Food and Drug Administration.

The cleanser formulation is readily prepared by combining the ingredients in a suitable vessel, with stirring or other agitation sufficient to form a substantially homogeneous mixture. In a preferred embodiment, the cleanser formulation is provided in a conventional foam-dispensing bottle (also known as a foaming bottle, foam pump, foam-dispensing pump, etc.). Activating the pump causes the cleanser formulation to mix with air as it passes through the pump nozzle, fine pores or mesh, and/or other mechanism. In combination, the air and surfactant(s) cause the cleanser formulation to foam as it is ejected from the bottle. The hydrogen peroxide may also facilitate foaming. While not bound by theory, it is believed that a foamed cleanser formulation has greater cleansing power than an unfoamed cleanser, and also has better "mouth feel."

The method of cleansing is suitable for use with all types of oral appliances, including orthodontic retainers, dental aligners (such as Invisalign® and ClearCorrect™ brand aligners), dentures, athletic mouth guards, snoring guards, sleep apnea appliances, tongue studs for pierced tongues, and other appliances commonly used in the mouth. In addition, the bleaching action of the hydrogen peroxide causes teeth, dental implants, dental crowns and bridges, and other dental prostheses to be whitened as the foamed cleanser formulation is applied, and the cleanser is further adapted to neutralize odors and kill pathogens that cause bad breath.

In a second aspect of the invention, a cleaning kit for a dental or other oral appliance is provided and includes a cleanser formulation as described above, contained within a foam-dispensing bottle. In one embodiment, the foam-dispensing bottle is housed in a fitted "holster," such as the type commonly used to hold a personal defense spray (mace). The holster can include a clasp, chain, and/or other fastener for attaching it to a keychain. This makes it very easy to carry the foam-dispensing bottle containing the cleanser formulation. Optionally, the cleaning kit also includes one or more oral appliance, of the type previously described. The kit can be distributed to a patient by a dentist or orthodontist at the time he or she provides the patient with an orthodontic retainer, aligner, or other dental appliance. It also can be distributed by stores that sell other types of oral appliances. This offers patients/consumers a convenient opportunity to purchase both a desired oral appliance and a cleanser formulation particularly adapted for use with the appliance.

Use of the method and cleaning kit permits the oral appliance wearer to enjoy the benefits of cleaning the appliance at regular intervals, or "as needed," without having to remove the appliance. This is particularly beneficial to persons who wear orthodontic retainers and similar dental appliances, as they often experience decreased salivary flow around the teeth while wearing the appliance. Free-flowing saliva bathes the teeth and increases the pH in the mouth, which counteracts bacterial acids that cause tooth decay and gum disease. The cleaning method and kit described herein foster the oral appliance wearer's oral hygiene by making it easy to clean the appliance regularly.

The invention includes a number of features, embodiments, advantages, and variations (some of which are described above). These include:

An oral care formulation designed to clean an oral appliance, such as a dental appliance, especially while the appliance is worn in the mouth, rather than by merely soaking the appliance or using it outside of the mouth.

An oral care formulation which, when used in the mouth, does not interfere with the function of the appliance. For example, if the appliance is moving teeth, the formulation will not interfere with the teeth moving.

An oral care formulation which, when used in the mouth, does not irritate hard or soft tissues of the mouth, including the teeth.

An oral care formulation that can be applied to dental appliances multiple times per day and at night, and before bedtime.

An oral care formulation that can be applied as a touch-up treatment to combat bad breath or appliance "funk" caused by the smell of saliva and other intraoral fluids.

An oral care formulation designed to kill bacterial flora that build up in or on the appliance while a person wears the appliance.

An oral care formulation that is easily applied to the entire inner surface area of the appliance that comes in contact with the teeth.

An oral care formulation that has adhesion properties that allow the formulation to adhere to the dental appliance, preventing it from falling out of the appliance prior to and when inserting the appliance in the mouth.

An oral care formulation that has properties that keep the formulation from sliding or moving from the place where the formulation was applied.

An oral care formulation which, when applied, reacts with organic stains, odors, food, saliva, and blood particles on the teeth, between teeth, between teeth and gums, between teeth and appliance, and within the microscopic porosity of the dental appliance materials (which are often fabricated from plastics, resins, composite materials, etc.).

An oral care formulation that activates when inserted into the mouth, moving the oral care formulation from room temperature to body temperature.

An oral care formulation that is dispensed from a container and applied to all surfaces of the dental appliance that interfaces with the teeth and gums.

An oral care formulation composed of either a one-chamber or a two-chamber system, and which, when dispensed, mixes.

A two-chamber system that combines an "a" and a "b" chemistry, which when combined activates the oral care formulation.

An oral care formulation that is activated under the pressure created by the sandwich formed between the dental appliance, oral care formulation, and the teeth and gums.

An oral care formulation containing a peroxide compound that releases oxygen as it decomposes, which agitates the formula's cleaning solvents and surfactants thereby enhancing the cleaning effects or action.

An oral care formulation containing a peroxide that releases free radicals as it decomposes, which whiten organic stain molecules found on the appliance and in the teeth enamel rods.

An oral care formulation containing a peroxide that releases free radicals and oxygen as it decomposes, which kills bacteria and biofilms located around the teeth, gums, and appliance.

An oral care formulation containing a peroxide that creates pressure as it decomposes, and moves some of the oral care formula into the mouth, which will kill bacteria that cause bad breath.

An oral care formulation packaged in containers that are portable or table top size.

An oral care formulation which, when dispensed, is a liquid, foam, gel, or powder.

An oral care formulation that whitens teeth.

An oral care formulation that kills intraoral bacteria that cause bad breath, tooth decay, and gum disease.

An oral care formulation that has a viscosity below 1000 centipoise, and ideally between 1 and 500 centipoise.

An oral care formulation containing one or more oxidizing agents from the following categories: hydrogen peroxide, carbamide peroxide, calcium peroxide, and magnesium peroxide.

An oral care formulation containing water over 20% of the total composition.

An oral care formulation containing alcohol ranging from 0.001% to 50%.

An oral care formulation containing one or more orally safe anionic surfactants, such as sodium lauryl sulphate, dodecyl sulfate, or sodium lauril sulphate, ranging from 0.001-30%.

An oral care formulation containing one or more surfactants from the class called zwitterionic surfactants, such as cocamidopropyl betaine, ranging from 0.001-30%.

An oral care formulation containing one or more surfactants from the class called poloxamers, such as poloxamer 407 and 338, and/or polysorbates, such as polysorbate 20, ranging from 0.001-30%.

An oral care formulation containing one or more non-ionic surfactants, such as alkyl polyglucosides, ranging from 0.001-40%.

An oral care formulation containing potassium hydroxide ranging from 0.001-10%.

An oral care formulation containing one or more chelating agents, such as ethylenediaminetetraacetic acid (EDTA), ranging from 0.001-10%.

An oral care formulation containing one or more flavorings such as mint, peppermint, cinnamon, spearmint, vanilla, orange, bubble gum, or wintergreen (methyl salicylate) ranging from 0.001-9%.

An oral care formulation containing citric acid ranging from 0.001-22%.

An oral care formulation containing food coloring.

An oral care formulation containing sodium bicarbonate.

An oral care formulation containing one or more sweeteners such as xylitol, aspartame, sucralose, sorbitol, or saccharine ranging from 0.001-30%.

An oral care formulation containing one or more fluorides in the form of acidulated, stannous, or sodium fluoride, ranging from 0.0001-5%.

An oral care formulation containing one or more compounds that remineralize teeth, such as ACP, calcium phosphate or other calcium chemicals.

An oral care formulation containing one or more cationic quaternary ammonium compounds, such as cetylpyridinium chloride, ranging from 0.001-3%.

An oral care formulation containing triclosan ranging from ranging from 0.001-5%.

An oral care formulation containing one or more ingredients to combat sensitive teeth, including potassium nitrate, potassium citrate, potassium chloride, stannous fluoride, and strontium chloride, ranging from 0.001-11%.

An oral care formulation containing one or more compounds or components to combat bad breath, such as chlorine dioxide, essential oils, and zinc chloride.

An oral care formulation containing one or more compounds or components to prevent tartar build-up on or in the appliance, such as pyrophosphate, hexametaphosphate, or zinc or zinc citrate.

An oral care formulation containing sorbitol ranging from ranging from 0.001-6%.

An oral care formulation containing propylene glycol, which is a solvent and/or humectant, ranging from ranging from 0.001-33%.

An oral care formulation containing disodium phosphate, which is a solvent and or humectant, ranging from ranging from 0.001-29%

An oral care formulation containing eucalyptol ranging from ranging from 0.001-3%.

An oral care formulation containing menthol ranging from ranging from 0.001-3%.

An oral care formulation containing thymol ranging from 0.001-3%.

Other modifications and variations may readily occur to those skilled in the art upon reading the present disclosure or seeing the invention in practice. It is intended that all such modifications and variations are included within the scope of the invention, which is limited only by the appended claims and equivalents thereof.

What is claimed is:

1. A method of cleaning an oral appliance while the appliance is in place in a person's mouth, comprising:
    introducing a quantity of a foamed cleanser formulation into the person's mouth, the cleanser formulation being directed onto the appliance;
    spraying the cleanser formulation in such a way that the cleanser formulation will reside between the appliance and the person's teeth, wherein the cleanser formulation is aimed close to areas of contact between the person's teeth and the appliance;
    keeping the cleanser formulation in the mouth for a desired amount of time; and
    expectorating any remaining cleanser formulation;
    wherein the cleanser formulation comprises a mixture of water, hydrogen peroxide, and at least one surfactant.

2. The method of claim 1, wherein the cleanser formulation is introduced into the person's mouth by dispensing it from a foam-dispensing bottle.

3. The method of claim 1, wherein the cleanser formulation comprises 70 to 98% water, 0.01 to 30% hydrogen peroxide, and 0.01 to 5% surfactant(s).

4. The method of claim 3, wherein the surfactant(s) is/are selected from the group consisting of sodium lauryl sulfate, sodium dodecyl sulfate, cocamidopropyl betaine, poloxamer 188, poloxamer 338, poloxamer 407, polysorbate 20, and alkyl polyglucosides.

5. The method of claim 3, wherein the cleanser formulation further comprises one or more additional ingredients selected from the group consisting of 0.01 to 4% sweetener(s), 0.01 to 4% ethylenediaminetetraacetate (EDTA), 0.01 to 6% sodium citrate or citric acid, and/or 0.01 to 3% flavorant(s).

6. The method of claim 5, wherein the cleanser formulation further comprises one or more additional ingredients selected from the group consisting of carbamide peroxide, calcium peroxide, magnesium peroxide, ethanol, potassium hydroxide, food coloring, sodium bicarbonate, acidulated fluoride, stannous fluoride, sodium fluoride, calcium phosphate, amorphous calcium phosphate (ACP), cetyl pyridinium chloride, triclosan, potassium nitrate, potassium citrate, potassium chloride, strontium chloride, anti-halitosis agent, tartar control agents, sorbitol, propylene glycol disodium phosphate, eucalyptol, menthol, and thymol.

7. The method of claim 1, wherein the oral appliance is selected from the group of appliances consisting of orthodontic retainers, dental aligners, dentures, athletic mouth guards, snoring guards, bleaching trays, and sleep apnea appliances.

8. The method of claim 1, wherein the foamed cleanser formulation has properties that keep the formulation from sliding or moving from the place where the foamed cleanser formulation was applied.

9. The method of claim 8, wherein the foamed cleanser formulation has a viscosity below 1000 centipoise.

10. The method of claim 9, wherein the foamed cleanser formulation has a viscosity between 1 and 500 centipoise.

* * * * *